(12) United States Patent
DiFilippo

(10) Patent No.: US 10,078,144 B2
(45) Date of Patent: Sep. 18, 2018

(54) OVERDETERMINED POSITRON EMISSION TOMOGRAPHY

(71) Applicant: THE CLEVELAND CLINIC FOUNDATION, Cleveland, OH (US)

(72) Inventor: Frank P. DiFilippo, Strongsville, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 133 days.

(21) Appl. No.: 14/990,170

(22) Filed: Jan. 7, 2016

(65) Prior Publication Data

US 2016/0195624 A1 Jul. 7, 2016

Related U.S. Application Data

(60) Provisional application No. 62/100,685, filed on Jan. 7, 2015, provisional application No. 62/166,262, filed on May 26, 2015.

(51) Int. Cl.
| | |
|---|---|
| *G01T 1/29* | (2006.01) |
| *G21K 1/02* | (2006.01) |
| *A61B 6/06* | (2006.01) |
| *A61B 6/03* | (2006.01) |
| *G01T 1/164* | (2006.01) |
| *A61B 6/00* | (2006.01) |

(52) U.S. Cl.
CPC ............ *G01T 1/2985* (2013.01); *A61B 6/037* (2013.01); *A61B 6/06* (2013.01); *A61B 6/4291* (2013.01); *A61B 6/508* (2013.01); *G01T 1/1648* (2013.01); *G21K 1/02* (2013.01); *A61B 6/5205* (2013.01)

(58) Field of Classification Search
CPC ......... A61B 6/037; A61B 6/06; A61B 6/4291; A61B 6/508; A61B 6/5205; G01T 1/1648; G01T 1/2985; G21K 1/02
See application file for complete search history.

(56) References Cited

U.S. PATENT DOCUMENTS

| | | | |
|---|---|---|---|
| 5,841,140 A * | 11/1998 | McCroskey | G01T 1/1642 250/363.03 |
| 6,373,059 B1 | 4/2002 | Stearns | |
| 2006/0180766 A1* | 8/2006 | Difilippo | G01T 1/1648 250/363.09 |
| 2008/0111081 A1 | 5/2008 | Chuang | |

(Continued)

OTHER PUBLICATIONS

Brooks, Rodney A., et al. "Design of a high resolution positron emissino tomograph: the Neuro-PET." Journal of computer assisted tomography 4.1 (1980):5-13.

(Continued)

*Primary Examiner* — Mark R Gaworecki
(74) *Attorney, Agent, or Firm* — Tarolli, Sundheim, Covell & Tummino LLP

(57) ABSTRACT

The present disclosure relates to increasing the spatial resolution of a clinical positron emission tomography (PET) scanner. The spatial resolution of the clinical PET scanner can be increased by placing a collimator, including a plurality of pinholes, inside the clinical PET scanner. Coincidence data of the annihilation photons are acquired by the PET scanner. A computer associates a pinhole location with the two detected locations of the coincident photons. All three locations are then used in the reconstruction of a high-resolution PET image.

25 Claims, 2 Drawing Sheets

(56) References Cited

U.S. PATENT DOCUMENTS

| | | | |
|---|---|---|---|
| 2010/0294941 A1 | 11/2010 | Chuang et al. | |
| 2011/0096970 A1* | 4/2011 | Vija ..................... | A61B 6/037 382/131 |
| 2012/0056095 A1 | 3/2012 | Metzler et al. | |

OTHER PUBLICATIONS

Kadrmas, Dan J., and Thomas C. Rust. "Convering slat collimators for PET imaging with large-area detectors." IEEE Transactions on Nuclear Science 50.1 (2003): 17-23.

Cardi, Christopher A., et al. "Pinhole PET (pPET): a multi-pinhole collimator insert for small animal SPECT imaging on PET cameras." IEEE Nuclear Science Symposium Conference Record, 2005. vol. 4. IEEE, 2005.

Cho, Z. H., et al. "High-resolution circular ring positron tomograph with dichotomic sampling: Dichotom-I." Physics in medicine and biology 28.11 (1983): 1219.

Cho, Z. H., et al. "Experimental results of the dichotomic sampling in circular ring positron emission tomograph." IEEE Transactions on Nuclear Science 30.3 (1983): 1892-1898.

Cho, Z. H., et al. "A new approach to very high resolution mini-brain PET using a small number of large detectors." IEEE Transactions on Nuclear Science 37.2 (1990): 842-851.

Difilippo, Frank P. "Enhanced PET resolution by combining pinhole collimation and coincidence detection." Physics in medicine and biology 60.20 (2015): 7969.

Goorden, Marlies C., et al. "VECTor: a preclinical imaging system for simultaneous submillimeter SPECT and PET." Journal of Nuclear Medicine 54.2 (2013): 306-312.

Tomograph, Whole-Body Positron Transaxial. "jni. U/Instrumentation and Physics." (1976).

Li, Yusheng, et al. "LOR-interleaving image reconstruction for PET imaging with fractional-crystal collimation." Physics in medicine and biology 60.2 (2015): 647.

Macdonald, L. R., et al. "Measured count-rate performance of the Discovery STE PET/CT scanner in 2D, 3D and partial collimation acquisition modes." Physics in medicine and biology 53.14 (2008): 3723.

Metzler, Scott D., Samuel Matej, and Joel S. Karp. "Resolution enhancement in PET reconstruction using collimation." IEEE transactions on nuclear science 60.1 (2013): 65-75.

Phelps, Michael E., et al. "ECAT: a new computerized tomographic imaging system for positron-emitting radiopharmaceuticals." Journal of nuclear medicine: official publication, Society of Nuclear Medicine 19.6 (1978): 635-647.

Shao, Yiping, et al. "Initial studies of PET-SPECT dual-tracer imaging." 2007 IEEE Nuclear Science Symposium Conference Record. vol. 6. IEEE, 2007.

Ter-Pogossian, Michel M., et al. "Super PETT I: a positron emission tomograph utilizing photon time-of-flight information." IEEE transactions on medical imaging 1.3 (1982): 179-187.

Yao, Rutao, Tianyu Ma, and Yiping Shao. "Lutetium oxyorthosilicate (LSO) intrinsic activity correction and minimal detectable target activity study for SPECT imaging with a LSO-based animal PET scanner." Physics in medicine and biology 53.16 (2008): 4399.

Yao, Rutao, et al. "Initial evaluation of LabPET/SPECT dual modality animal imaging system." IEEE Transactions on Nuclear Science 60.1 (2013): 76-81.

Yao, Rutao, et al. "Multipinhole SPECT helical scan parameters and imaging volume." Medical physics 42.11 (2015): 6599-6609.

PCT International Search Report and Written Opinion for PCT/US2016/012443, dated Apr. 25, 2016, pp. 1-15.

* cited by examiner

OVERDETERMINED POSITRON EMISSION TOMOGRAPHY

RELATED APPLICATIONS

This application claims priority to each of U.S. Provisional Patent Application Ser. No. 62/100,685, filed Jan. 7, 2015, and U.S. Provisional Patent Application Ser. No. 62/166,262, filed May 26, 2015. Each of these applications are hereby incorporated by reference.

TECHNICAL FIELD

The present disclosure relates generally to positron emission tomography (PET) and, more specifically, to systems and methods that can increase the spatial resolution of clinical PET scanners.

BACKGROUND

Positron emission tomography (PET) is a functional imaging modality used in both clinical and laboratory settings. A PET image can show the distribution of a tracer throughout a subject's body. The tracer can be labeled with a radionuclide that emits positrons upon decay. The positrons can contact electrons and annihilate and produce pairs of 511 keV photons traveling in opposite directions. A PET scanner can detect coincident photons arising arise from the same annihilation and store these coincident events in arrays corresponding to projections through the subject's body or in a list of information specifying each event ("list mode"). A PET image can be reconstructed using standard tomographic techniques to reveal the function of various tissues (e.g., cells, organs, tissues, etc.) of a subject's body within the field of view of the PET scanner.

The functions that can be revealed in the PET image can be dependent on the spatial resolution of the PET scanner, which can be determined based on the ability of detectors within the PET scanner to locate a detected event. Clinical PET scanners designed to image human subjects can produce images with a spatial resolution of about 4.5 cm. While such a spatial resolution is generally acceptable for most clinical applications, it can be insufficient for some clinical applications requiring high spatial resolution in a focused region of interest (e.g. prostate imaging or breast imaging). This spatial resolution is often unacceptable for laboratory research, especially research involving small animals (e.g., rodents). Accordingly, dedicated small animal PET scanners have been developed for laboratory research applications using special higher-resolution detectors to achieve a spatial resolution of about 1.5 mm. However, such small animal PET scanners can be prohibitively expensive and require additional facilities.

SUMMARY

The present disclosure relates generally to positron emission tomography (PET). Clinical PET scanners do not provide the spatial resolution necessary for imaging small areas (e.g., for small animal imaging studies). Although specialized small animal PET scanners can provide the desired spatial resolution for small animal imaging, these small animal PET scanners are often prohibitively expensive and require additional facilities, often making them impractical. Accordingly, the systems and methods of the present disclosure can increase the spatial resolution of a clinical PET scanner by employing a collimator that includes a plurality of pinholes to achieve pinhole-assisted PET.

In one aspect, the present disclosure includes a system that can increase the spatial resolution of a clinical positron emission tomography (PET) scanner. The system can include the clinical PET scanner designed primarily for imaging human subjects. The system can also include a collimator assembly proportioned to rest on a patient bed associated with the clinical PET scanner. The collimator assembly can include a plurality of pinholes. The system can also include a test bed mechanically coupled to the collimator assembly and adapted to support a test subject. The clinical PET scanner can be configured to acquire collimated data and non-collimated data to create an image based on the collimated data and the non-collimated data. The image can have a spatial resolution less than 4 mm.

In another aspect, the present disclosure includes a method for creating a PET image with an increased spatial resolution compared to a PET image from a clinical PET scanner alone. A subject can be positioned within a collimator proportioned to rest on a patient bed associated with a clinical PET scanner. The collimator can include a plurality of pinholes. High-resolution/high-noise data can be acquired from the subject with the clinical PET scanner plus the collimator. Low-resolution/low-noise data also can be acquired from the subject with the clinical PET scanner away from the collimator. An image can be created based on the high-resolution/high-noise data and the low-resolution/low-noise data. The image can have a spatial resolution less than 4 mm.

In a further aspect, the present disclosure includes a device proportioned to rest on a patient bed associated with a clinical PET scanner. The device can include a hollow collimator assembly constructed of a thin plastic material and including a plurality of pinholes. Each of the plurality of pinholes can be filled with a metal insert. The collimator can be proportioned to rest on the patient bed associated with the clinical PET scanner and comprising a plurality of pinholes. A test bed can be mechanically coupled to the collimator assembly and adapted to support a test subject. The can be configured to move from inside the collimator assembly to outside the collimator assembly.

In a further aspect, the present disclosure describes geometric calibration methods for pinhole imaging. Image reconstruction requires accurate knowledge of the location and orientation of each pinhole with respect to the scanner coordinate system. The standard approach to calibrating the geometry is to scan point sources and estimate geometric parameters from the data. An additional approach is to derive this information from the coincidence data itself, without performing a separate point source scan or acquiring point source data simultaneously with the object being scanned. In this aspect, the coincident lines of response accumulate strongly at the pinhole location and also reveal the orientation of the pinhole.

In a further aspect, the coincidence data are used to accept or reject events prior to image reconstruction. The standard approach to pinhole imaging is to employ sufficient shielding to ensure that a plurality of recorded events passed through the pinhole. For 511 keV photons, the shielding requirements are significant, resulting in heavy and unwieldy collimators. Alternatively, the coincidence data provide valuable information that greatly reduces the shielding requirements. The coincident line of response specifies a distance and angle of incidence relative to the pinhole location and orientation. Based on the pinhole design, distance and angular thresholds are set in order to accept or reject the event for image reconstruction. Furthermore, when using a time-of-flight PET scanner, the relative timing between the detected coincident photons also helps specify acceptance or rejection of the event.

In a further aspect, the coincidence information is used to associate each event with a specific pinhole. Standard multi-pinhole imaging can include multiplexing, where photons passing through different pinholes are recorded at the same detector coordinates and cannot be distinguished. Pinhole collimators are designed to minimize or avoid multiplexing by carefully specifying pinhole location, orientation, and angular cut-off and by introducing additional shielding to block detection of multiplexed events. However in this aspect, the distance between the coincidence line of response and each pinhole provides valuable information that can specify the pinhole through which the event passed. This approach allows for a large number of pinholes without the deleterious effect of multiplexing.

In a further aspect, the pinhole collimation avoids errors from non-collinearity of annihilation photons. In PET, it is assumed that the photons are traveling in opposite directions. However the photons are actually non-collinear (by approximately 0.5 degree), which introduces error in image reconstruction and limits spatial resolution. By introducing pinholes along with coincidence detection, the error from non-collinearity is avoided, allowing for improved spatial resolution.

In a further aspect, the pinhole collimator can be retracted to perform coincidence PET imaging without pinholes. This flexibility is valuable when low noise images (albeit with low spatial resolution) are desirable, for example in dynamic PET imaging. In addition, a retractable collimator allows for sequential acquisition of PET data alone and of PET data combined with pinholes.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
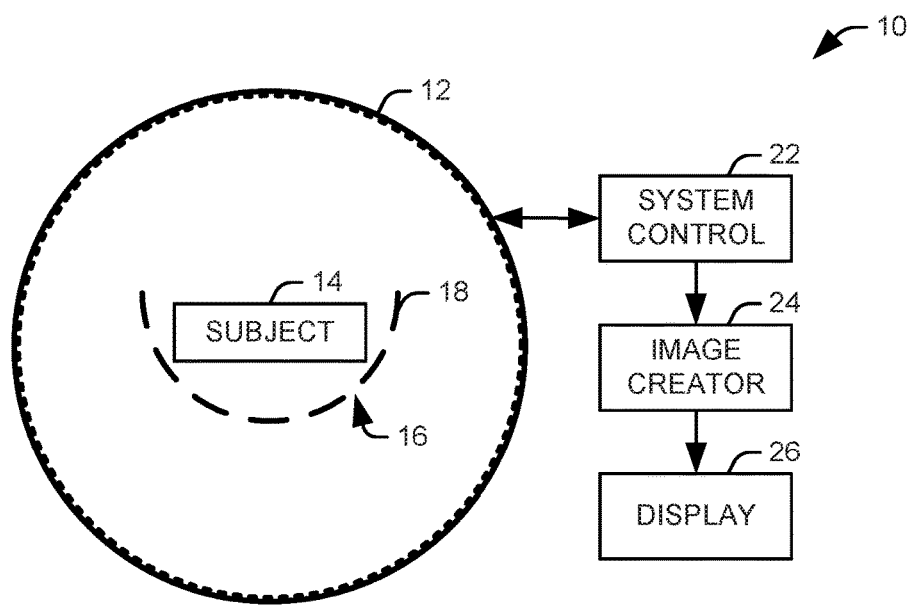
FIG. 1 is a schematic block diagram showing a system that can create a small animal positron emission tomography (PET) image in accordance with an aspect of the present disclosure.

In the context of the present disclosure, the singular forms "a," "an" and "the" can also include the plural forms, unless the context clearly indicates otherwise. The terms "comprises" and/or "comprising," as used herein, can specify the presence of stated features, steps, operations, elements, and/or components, but do not preclude the presence or addition of one or more other features, steps, operations, elements, components, and/or groups. As used herein, the term "and/or" can include any and all combinations of one or more of the associated listed items. Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "positron emission tomography (PET)" can refer to a functional imaging modality used in both clinical and laboratory settings that can generate an image revealing a function of a subject's body (e.g., detecting chemical processes and/or biological processes). For example, the function can be revealed based on a distribution of a tracer throughout at least a portion of the subject's body (e.g., based on the field of view of the PET scanner). In some instances, functional PET imaging and structural computed tomography (CT) imaging can be performed together to create a three-dimensional image of the structure of a portion of the subject's body overlaid with a functional image of the same portion of the subject's body.

As used herein, the term "tracer" can refer to a biologically active molecule that can distribute throughout a subject's body and collect in areas with higher chemical activity and/or biological activity. The tracer can be labeled with a short-lived radioactive molecule that can emit positrons upon decay. For example, the tracer can be introduced into the subject's body through injection, swallowing, or inhalation based on the tissue being studied.

As used herein, the term "positron" can refer to the antimatter counterpart of an electron. A positron has the same mass as an electron, an electric charge of +1 e, and a spin of ½. When a positron collides with an electron, annihilation can occur, resulting in the production of two 511 keV photons that travel in opposite directions.

As used herein, the term "gamma photons" can refer to the two high energy photons (e.g., 511 keV) arising from positron annihilation due to radioactive decay. The two gamma photons can be detected by detectors of a PET scanner, facilitating PET imaging.

As used herein, the term "coincidence" can refer to the simultaneous detection of two or more photons at different PET detectors. In some instances (e.g., "time-of-flight PET"), the number of coincidence events occurring between the PET detectors can indicate the level of radioactivity on the line of response (LOR) through the subject between the detectors.

As used herein, the term "field of view" can refer to an area visible to the camera of a PET scanner.

As used herein, the term "spatial resolution" can refer to a measure of an ability of the PET scanner to clearly depict variations in the distribution of the tracer within the field of view of the subject. In some instances, the spatial resolution can depend on the size of the detectors. For example, the spatial resolution can be greatest at the center of the field of view and worsen toward the edges of the FOV.

As used herein, the term "collimation" can refer to the use of a perforated absorber (e.g., a "collimator") to restrict the field of view of a detector and reduce scatter. In some instances, the perforations can be "pinholes."

As used herein, the term "clinical" can refer to the observation or treatment of a human patient. Accordingly, for example, a "clinical PET scanner" can refer to a PET scanner intended for the imaging of a human patient.

As used herein, the term "substantially the same time" can refer to two events occurring at the exact same time or at approximately the same time, which is dependent on the electronic timing accuracy of the PET detectors. For example, two events occurring at approximately the same time can be separated by 5 nanoseconds or less. As another example, two events occurring at approximately the same time can be separated by 2 nanoseconds or less. In another example, two events occurring at approximately the same time can be separated by 1 nanosecond or less. As a further example, two events occurring at approximately the same time can be separated by 0.5 nanoseconds or less. As still a further example, two events occurring at approximately the same time can be separated by 0.2 nanoseconds or less. As timing accuracy improves, the ability to localize the radioactivity along the line of response also improves ("time of flight" PET).

As used herein, the term "subject" can refer to any animal undergoing a PET imaging study. In some instances, the subject can be any research small animal undergoing a PET imaging study, including, but not limited to, a mouse, a rat, a dog, a cat, etc. In other instances, the subject can be a human being or other large animal, undergoing a PET imaging study on a small body part (e.g., a hand or a wrist).

II. Overview

The present disclosure relates generally to positron emission tomography (PET). The systems and methods of the present disclosure can increase the spatial resolution of clinical PET scanners to a level comparable to that of a specialized small animal PET scanner, saving both money and space. Accordingly, the systems and methods of the present disclosure can employ a collimator that includes a plurality of pinholes to achieve pinhole-assisted PET to increase the spatial resolution of a clinical PET scanner.

III. Systems

One aspect of the present disclosure can include a system that can create a small animal positron emission tomography (PET) image. The system 10 can utilize three locations (coincidence detection of a pair of photons plus location of a pinhole) to determine the line of response. This is different than traditional PET imaging, which uses two locations (coincidence detection of a pair of photons). Accordingly, the pinhole-assisted PET can provide high-resolution PET imaging for small animal research using a clinical scanner. Pinhole-assisted PET provides a significant cost advantage compared to dedicated small animal PET, high resolution using clinical PET detectors comparable to that of dedicated small animal PET, no need for complete shielding resulting in simpler collimator design and hardware, the ability to acquire high resolution, low sensitivity pinhole assisted PET and low resolution high sensitivity PET images at the same time, and compared to "virtual pinhole" PET there is no need for external high resolution detectors and specialized electronics to interface with the clinical scanner. One example of such a system 10 that can create a small animal PET image is shown in FIG. 1.

Figure 2:
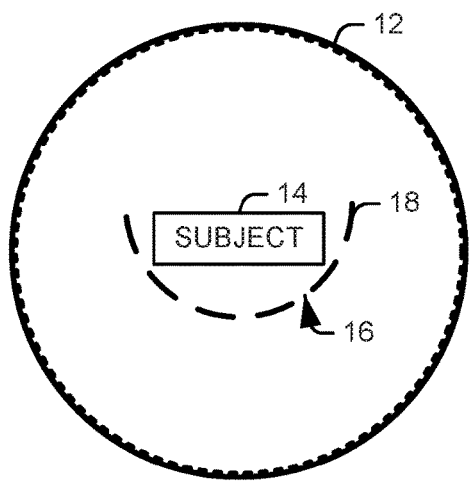
FIG. 2 is a schematic block diagram of an exemplary device that can employ the system in FIG. 1 with the small animal inside the collimator.
Figure 3:
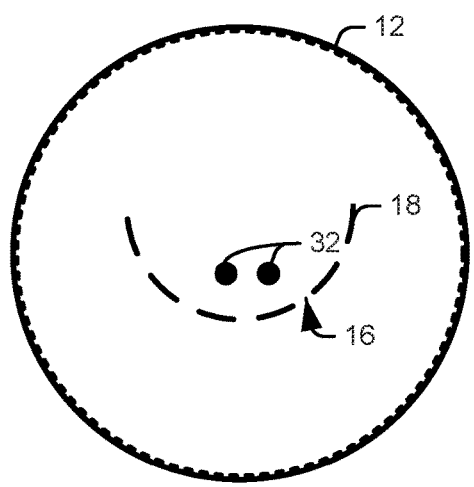
FIG. 3 is a schematic diagram showing an example configuration of the system in FIG. 1 with point sources inside the collimator.
Figure 4:
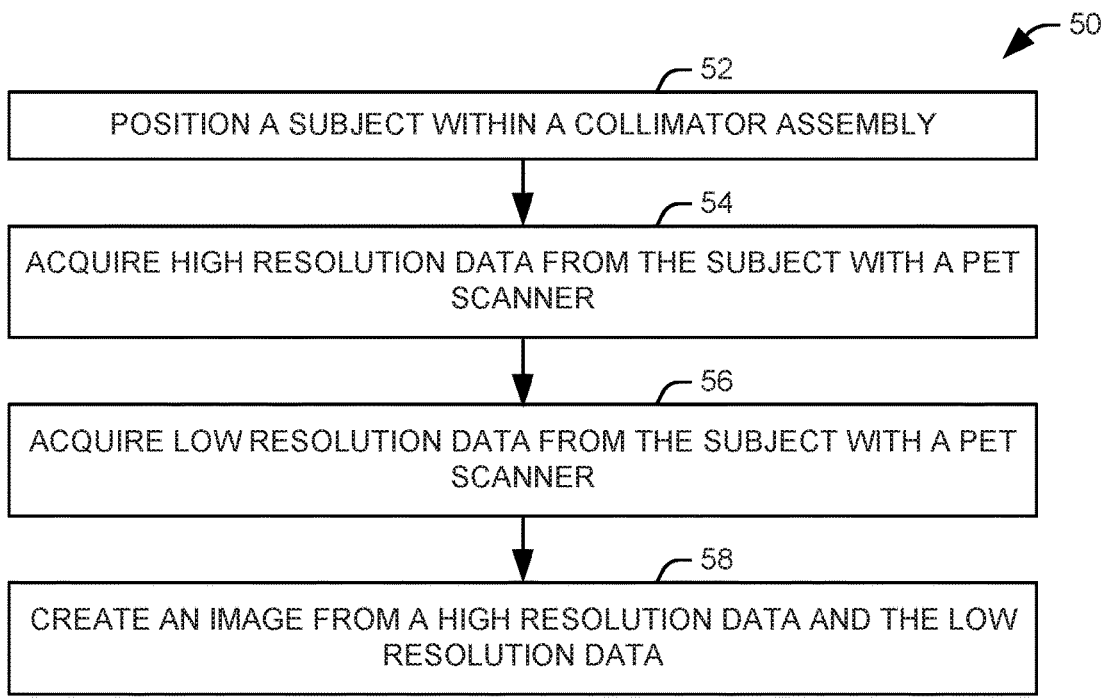
FIG. 4 is a process flow diagram illustrating a method for creating a small animal PET image according to another aspect of the present disclosure.

FIG. 1 illustrates an example of a system 10 that can create a small animal PET image, according to an aspect of the present disclosure. FIG. 1, as well as associated FIGS. 2-4, are schematically illustrated as block diagrams with the different blocks representing different components. The functions of one or more of the components can be implemented by computer program instructions. Additionally, some functionalities not illustrated can be implemented by computer program instructions.

These computer program instructions can be provided to a processor of a general purpose computer, special purpose computer, and/or other programmable data processing apparatus to produce a machine, such that the instructions, which execute via the processor of the computer and/or other programmable data processing apparatus, create a mechanism for implementing the functions of the components specified in the block diagrams.

These computer program instructions can also be stored in a non-transitory computer-readable memory that can direct a computer or other programmable data processing apparatus to function in a particular manner, such that the instructions stored in the non-transitory computer-readable memory produce an article of manufacture including instructions, which implement the function specified in the block diagrams and associated description.

The computer program instructions can also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions of the components specified in the block diagrams and the associated description.

Accordingly, the system 10 described herein can be embodied at least in part in hardware and/or in software (including firmware, resident software, micro-code, etc.). Furthermore, aspects of the system 10 can take the form of a computer program product on a computer-usable or computer-readable storage medium having computer-usable or computer-readable program code embodied in the medium for use by or in connection with an instruction execution system. A computer-usable or computer-readable medium can be any non-transitory medium that is not a transitory signal and can contain or store the program for use by or in connection with the instruction or execution of a system, apparatus, or device. The computer-usable or computer-readable medium can be, for example but not limited to, an electronic, magnetic, optical, electromagnetic, infrared, or semiconductor system, apparatus or device. More specific examples (a non-exhaustive list) of the computer-readable medium can include the following: a portable computer diskette; a random access memory; a read-only memory; an erasable programmable read-only memory (or Flash memory); and a portable compact disc read-only memory.

As shown in FIG. 1, one aspect of the present disclosure can include a system 10 configured to create a small animal PET image. The system 10 can include a scanning assembly configured to record an image of a patient (e.g., a human patient). The system 10 can be configured for imaging a small laboratory test subject 14 with detectors 12 primarily designed to image patients larger than the small laboratory test subjects. The scanning assembly can include at least two detectors 12 that are operative to detect radiation emitted from a patient. In some instances, the scanning assembly can include tens or hundreds of detectors and thousands of scintillation crystals comprising a full ring. For example, the detectors 12 can include any appropriate detector for detecting radiation from a patient, such as nuclear detectors that detect radiation emitted from the patient, radiological imaging devices (e.g., for computed tomography) that irradiate the patient and detect attenuation of the radiation as it passes through the subject, or a combination of multiple detector types. In one implementation, the scanning assembly can be a PET system with detectors 12 configured to detect 511 keV photons. In other implementations, the scanning assembly can be a PET/computed tomography system with detectors 12 that include gamma photon detectors configured to detect 511 keV photons and detectors that detect attenuation of radiation as it passes through the subject. For example, a tracer can be introduced into the subject's body through injection, swallowing, or inhalation based on the tissue being studied, and the tracer can emits a pair of 511 keV photons upon decay.

To image patients, the detectors 12 can be configured with a spatial resolution greater than 4 mm. A system control 22 can interface with the detectors to receive an indication of a detection of the radiation. The system control 22 can isolate coincident detections from the two detectors 12 at substantially the same time and pass information about the coincident detections to the image creator 24. The image creator 24 can create an image based on a plurality of coincident detections and pass the image to the display 26. The system control 22 can move the detectors 12 around the patient to detect the coincident emissions of radiation at different points around the patient's body.

However, this spatial resolution is not sufficient for imaging a small laboratory test subject 14. Accordingly, the spatial resolution must be corrected in order to produce images of the small laboratory test subject 12. The small laboratory test subject 14 can be placed within a collimator assembly 18 (e.g., on a test bed mechanically coupled to the collimator assembly), and the collimator assembly can be placed on the bed configured to hold the patient. The collimator assembly 18 can have a plurality of pinholes 16 to provide pinhole-collimation. For example, each of the pinholes 16 can have a radius that is less than 5 cm (e.g., if the radius of the PET scanner is 400 cm). As another example, each of the pinholes 16 can have a radius that is less than 4 cm. As another example, each of the pinholes 16 can have a radius that is less than 2.5 cm. In one implementation, the collimator assembly 18 is configured to collimate 511 keV photons.

In some instances, the collimator assembly 18 can be hollow and constructed of a thin plastic material. In other instances, plurality of pinholes 16 can be filled with small inserts (e.g., metal inserts, like tungsten). In the illustrated example, the collimator assembly 18 is implemented as a tungsten structure shaped as an annular segment, the walls of which contain a plurality of pinhole apertures. In still other instances, the collimator assembly 18 can be mechanically coupled to a test bed, which can be configured to move from inside the collimator assembly to outside the collimator assembly. In some instances, the bed can be rotatable within the collimator assembly 18. In other instances, the collimator assembly 18 can be rotatable. It will be appreciated that the configuration of the collimator assembly can be adjusted to improve the quality (e.g., resolution, scope, or magnification) of the imaging of the subject. For example, the position of the collimator assembly, relative to at least one of the subject and the at least one detector, can be adjusted or the configuration of the pinholes in the collimator assembly can be changed as to alter the scope and magnification associated with the image.

With the collimator, the system control 22 can acquire both collimated data and non-collimated data, and the image creator 24 can create an image based on the collimated data and the non-collimated data. For example, the image creator 24 can create the image based on a maximum-likelihood algorithm of the collimated data and the non-collimated data. In another example, the image creator 24 can create the image based on a weighted algorithm of the collimated data and the non-collimated data. In some instances, the image creator 24 can be configured to acquire collimated data and non-collimated data to create an image based on the collimated data and the non-collimated data with a spatial resolution less than 4 mm. In other instances, the image creator 24 can be configured to acquire collimated data and non-collimated data to create an image based on the collimated data and the non-collimated data with a spatial resolution less than 3 mm. In still other instances, the image creator 24 can be configured to acquire collimated data and non-collimated data to create an image based on the collimated data and the non-collimated data with a spatial resolution less than 2 mm. In still further instances, the image creator 24 can be configured to acquire collimated data and non-collimated data to create an image based on the collimated data and the non-collimated data with a spatial resolution less than 1 mm. As an example, the pinhole can provide about 1.5 mm resolution from close to the small laboratory animal test subject 14 and the detectors alone can provide about 4 mm resolution from far away from the small laboratory animal test subject. Thus, the effect of the detector's poor resolution is minimized near the pinhole and the error from photon non-collinearity is minimized because of the pinhole.

In some instances, as shown in FIGS. 2 and 3, the collimated data and the non-collimated data can be acquired at different times. In FIG. 2, the small animal is under the pinholes and collimated data is acquired. The collimated data can be used to produce high-resolution/high-noise images. In FIG. 3, the animal is removed from the pinholes and replaced by one or more point sources 32 under the pinholes and non-collimated data is acquired. The non-collimated data can be used to produce low-resolution/low noise images. Image processing and deconvolution can be used to get the best images (e.g., by weighted least squares combination).

For example, the point sources 32 can include liquid 18F and/or long-lived 22Na source. It will be appreciated, however, one or more radio-opaque markers could be used in combination with or in place of the at least one radiation point sources 32 to accommodate other detector types (e.g., detectors primarily designed for CT). The scan data related to the at least one point source 32 can be utilized to generate one or more calibration parameters for the system.

In some instances, the point sources can be scanned separately to calibrate the geometry. In other instances, the coincidence data itself can be used to derive the system geometry (auto-calibration). The auto-calibration can be based on backprojected emission data, which can reveal the point source locations and orientations relative to the image coordinate system. A global fit to the scan-specific subset of geometric parameters can be performed using an image-based metric. Specifically, if the directional intensity of the backprojection-based auto-calibration is insurmountable, the fallback is to acquire a rapid point source scan sufficient to determine the subset of geometric parameters.

In other instances, the collimated data and the non-collimated data can be acquired at substantially the same time. The data can be combined within an image processing algorithm, being careful to reject LOCs that intersect the pinhole inserts. In some instances, a calibration marker (e.g., a point source of radiation smaller in volume and more active than the test subject so that it appears as a small, bright point at the detector 12) can be mounted to the test bed associated with the test subject 14.

IV. Methods

Another aspect of the present disclosure can include a method for creating a small animal positron emission tomography (PET) image. One example of such a method 50 is shown in FIG. 4.

The method 50 is illustrated as a process flow diagram with flowchart illustrations. For purposes of simplicity, the method 50 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 50.

One or more blocks of the respective flowchart illustrations, and combinations of blocks in the block flowchart illustrations, can be implemented by computer program instructions. These computer program instructions can be stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, the steps/acts can be implemented by a system comprising a processor that can access the computer-executable instructions that are stored in a non-transitory memory.

The method 50 of the present disclosure may be embodied in hardware and/or in software (including firmware, resident software, micro-code, etc.). Furthermore, aspects of the present disclosure may take the form of a computer program product on a computer-usable or computer-readable storage medium having computer-usable or computer-readable program code embodied in the medium for use by or in connection with an instruction execution system. A computer-usable or computer-readable medium may be any non-transitory medium that can contain or store the program for use by or in connection with the instruction or execution of a system, apparatus, or device.

As shown in FIG. 4, the method 50 can be utilized for creating a small animal PET image. At 52, a subject (e.g., subject 14) can be positioned within a collimator (e.g., collimator 22) comprising a plurality of pinholes (e.g., pinholes 16). In some instances, the collimator can be proportioned to rest on a patient bed associated with a clinical positron emission tomography (PET) scanner.

At 54, high-resolution/high-noise data can be acquired from the subject with the clinical PET scanner. At 56, low-resolution/low-noise data can be acquired from the subject with the clinical PET scanner. In some instances, the subject can be removed from the collimator assembly before acquiring the low-resolution/low-noise data from the subject with the clinical PET scanner. For example, the subject can be replaced with point sources to calibrate the collimator. In other instances, the high-resolution/high-noise data and the low-resolution/low-noise data can be acquired at substantially the same time from the same collimator.

At 58, an image can be created based on the high-resolution/high-noise data and the low-resolution/low-noise data. For example, the image can exhibit a spatial resolution less than 4 mm. In another example, the image can exhibit a spatial resolution less than 3 mm. In yet another example, the image can exhibit a spatial resolution less than 2 mm. In still another example, the image can exhibit a spatial resolution less than 1 mm.

Three locations (coincidence detection of a pair of gamma photons and a location of the collimator assembly) can be utilized to determine a line of response for creating the image. In some instances, the image can be created based on a weighted least squares algorithm of the high-resolution/high-noise data and the low resolution/low noise data. In other instances, the image can be created based on a maximum-likelihood algorithm of the high-resolution/high-noise data and the low resolution/low noise data.

Figure 5:
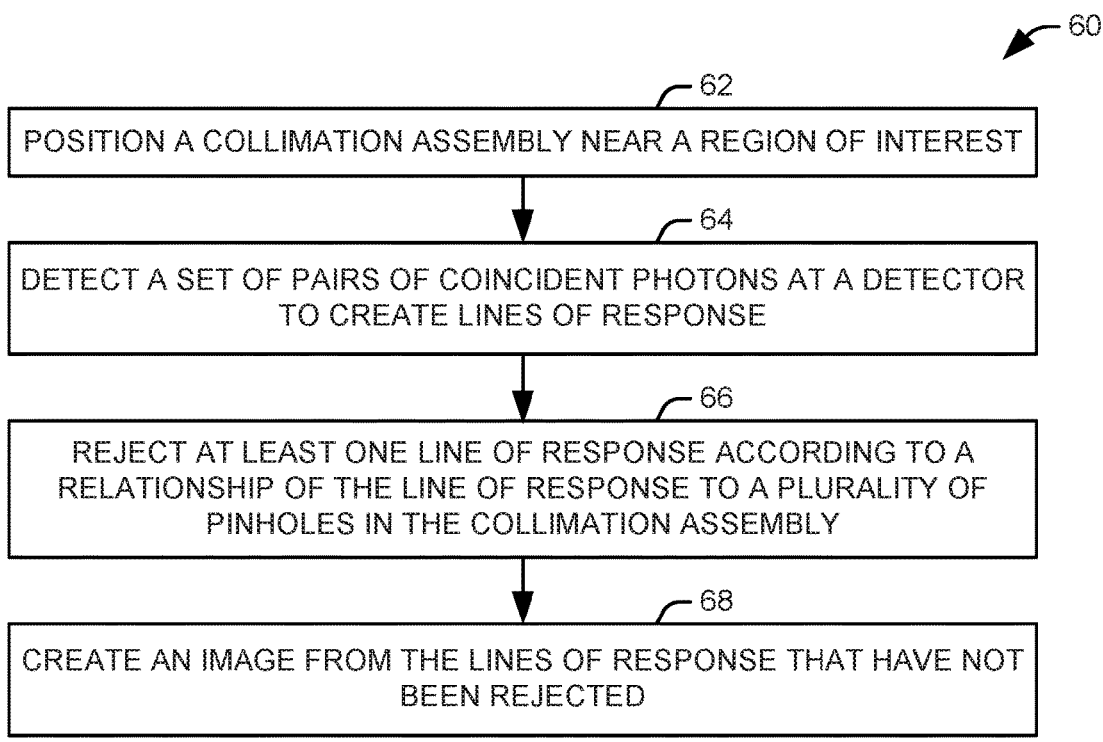
FIG. 5 illustrates a method for imaging a region of interest with a clinical positron emission tomography (PET) scanner.

FIG. 5 illustrates a method 60 for imaging a region of interest with a clinical positron emission tomography (PET) scanner. At 62, a collimation assembly is positioned in close proximity to the region of interest. Specifically, the collimation assembly is positioned to be closer to the region of interest than a detector or detectors associated with the PET scanner. The collimator can include a plurality of pinholes. In one implementation, the collimator can be mounted to or rest upon a patient bed of the clinical PET scanner. In another implementation, the collimator is inserted into a test subject as part of a probe. When the collimation assembly is positioned, point sources can be placed at known locations within the collimator assembly to allow for calibration the collimator assembly.

At 64, a set of pairs of coincident photons are detected at the detector associated with the PET scanner to determine a corresponding set of lines of response. A line of response (LOR), as has been discussed previously, is a projected line connecting the position on the detector at which the first photon of a pair of coincident photons is detected to the position on the detector at which the second photon of the pair is detected. It will be appreciated that the line of response may not be a true line due to moderate non-collinearity errors associated with PET scanning. In one implementation, multiple sets of LOR data can be detected, with a first set utilizing the collimator assembly and second set not using the collimator assembly. The sets can be taken simultaneously, with lines of response not passing through the collimator assembly used for the second set. Alternatively, the second set of data can be taken with the collimator removed.

At 66, at least one line of response of the set of respective lines of response is rejected according to relationship of each line of response to the plurality of pinholes. Specifically, a given line can be rejected if it is not likely to have passed through one of the pinholes in the collimator. To this end, the line can be rejected if a distance of closest approach of the LOR from the pinhole exceeds a threshold and/or an angle of incidence of the line of response with respect to the pinhole orientation exceeds a threshold value. It will be appreciated that the positions and orientations of the pinholes can be known a priori or determined via a separate calibration process. In one implementation, locations and orientations of the plurality of pinholes can be estimated from a backprojected image formed from the plurality of lines of response that have not been rejected.

At 68, an image is created, based on a plurality of lines of response that have not been rejected. In one implementation, only the high resolution data, represented by the non-rejected LORs that pass through the pinholes, can be used to generate the image. In another implementation, both the high resolution data and low resolution data captured without the collimator can be used. In this implementation, the image can be generated via a weighted algorithm of data derived from the collimated and non-collimated lines of response. Alternatively, the image can be created based on a maximum-likelihood algorithm performed on the collimated and non-collimated data. This image can then be displayed to a user and/or stored on a tangible medium.

In one implementation, detection events were processed according to the coincidence information and the known geometry of the pinholes. The line of response (LOR) defined by the two crystals of interaction was examined as to whether a photon was likely to have passed through the pinhole. The criteria for acceptance were that the distance between the LOR and the pinhole was within 4 mm (PET spatial resolution) and that the angle between the LOC and the pinhole normal vector was within 15° (pinhole cone half-angle plus an allowed tolerance). If the LOR was outside either of these ranges, the coincidence event was rejected.

Accepted coincidence events were histogrammed into pinhole-specific projections according to the crystals of detection at the detector. The pinhole associated with the coincidence event was assigned according to proximity to the LOR. Since the spacing between pinholes was significantly larger than the PET resolution, the pinhole assignment was unambiguous. This pinhole-specific event processing avoids overlapping projections which would have occurred with conventional multi-pinhole SPECT acquisition. Accordingly, each event can be evaluated according to the location of detection of each of the coincident photons as well as the location of its associated pinhole from the collimator.

From the above description, those skilled in the art will perceive improvements, changes and modifications. Such improvements, changes and modifications are within the skill of one in the art and are intended to be covered by the appended claims.

What is claimed is:

1. A system for imaging a region of interest comprising:
a positron emission tomography (PET) scanner comprising at least one detector configured for detection of temporally coincident photons;
a collimation assembly, having a plurality of apertures, placed such that the collimation assembly is closer to the region of interest than the at least one detector;
an image creator configured to detect a set of pairs of coincident photons at the detector associated with the PET scanner to determine a corresponding set of lines of response for the set of pairs of coincident photons, determine which of the plurality of apertures that a photon of a pair of coincident photons passed through from the line of response corresponding to the pair of coincident photons, reject at least one line of response of the set of respective lines of response according to the relationship of each line of response to the plurality of apertures, and generate an image of the region of interest from the plurality of lines of response that have not been rejected.

2. The system of claim 1, wherein the collimator assembly comprises a collimator mounted to one of a gantry of the scanner and a bed of the scanner.

3. The system of claim 1, wherein the collimator assembly comprises a collimator on a removable device.

4. The system of claim 3, wherein the removable device rests on a bed of the scanner.

5. The system of claim 1, wherein the plurality of apertures of the collimator assembly comprises a plurality of pinholes configured to project a magnified view of the region of interest onto at least one region of the at least one detector.

6. The system of claim 1, wherein the collimator assembly comprises a mechanism that removes a collimator from the scanner and reintroduces the collimator to the scanner.

7. The system of claim 1, wherein the collimator assembly comprises a mechanism that mechanically steps or rotates a collimator for improved data sampling.

8. The system of claim 1, wherein the collimator assembly is configured to collimate 511 keV photons.

9. A method for imaging a region of interest with a positron emission tomography (PET) scanner comprising:
positioning a collimation assembly such that the collimation assembly is closer to the region of interest than a detector associated with the PET scanner, the collimation assembly comprising a plurality of apertures;
detecting a first set of pairs of coincident photons at the detector associated with the PET scanner to determine a corresponding first set of lines of response;
rejecting at least one line of response of the first set of respective lines of response according to the relationship of each line of response of the first set of lines of response to the plurality of apertures;
detecting a second set of pairs of coincident photons at the detector associated with the PET scanner assembly to determine a corresponding second set of lines of response that do not pass through the collimation assembly; and
creating an image based on a plurality of lines of response that have not been rejected and the second set of lines of response.

10. The method of claim 9, wherein detecting a second set of pairs of coincident photons at the detector comprises acquiring the second set of pairs of coincident photons without the collimation assembly.

11. The method of claim 10, wherein the image is created based on a weighted algorithm of data derived from the plurality of lines of response that have not been rejected and data derived from the second set of lines of response.

12. The method of claim 9, wherein the plurality of lines of response that have not been rejected and the second set of lines of response are acquired at substantially the same time.

13. The method of claim 12, wherein the image is created based on a maximum-likelihood algorithm of data derived from the plurality of lines of response that have not been rejected and data derived from the second set of lines of response.

14. The method of claim 9, further comprising placing point sources within the collimation assembly to calibrate the collimation assembly.

15. The method of claim 9, further comprising estimating locations and orientations of the plurality of apertures from a backprojected image formed from the set of lines of response.

16. The method of claim 9, wherein positioning the collimation assembly comprises inserting a probe into a test subject.

17. The method of claim 9, wherein rejecting at least one line of response of the set of respective lines of response according to relative positions of each line of response and the plurality of apertures comprises rejecting the at least one line of response according to at least one of a distance from an aperture and an angle of incidence of the at least one line of response with respect to an aperture orientation.

18. The method of claim 9, wherein rejecting at least one line of response of the set of respective lines of response further comprises rejecting at least one line of response according to a difference in a detection time between a first photon of a corresponding pair of coincident photons and a second photon of the pair of coincident photons.

19. The method of claim 9, further comprising determining which of the plurality of apertures that a photon of a pair of coincident photons passed through from the line of response corresponding to the pair of coincident photons.

20. A method for imaging a region of interest with a positron emission tomography (PET) scanner comprising:
    positioning a collimation assembly such that the collimation assembly is closer to the region of interest than a detector associated with the PET scanner, the collimation assembly comprising a plurality of apertures;
    detecting a set of pairs of coincident photons at the detector associated with the PET scanner to determine a corresponding set of lines of response;
    estimating locations and orientations of the plurality of apertures from a backprojected image formed from the set of lines of response;
    rejecting at least one line of response of the set of respective lines of response according to the relationship of each line of response to the plurality of apertures; and
    creating an image based on a plurality of lines of response that have not been rejected.

21. The method of claim 20, wherein the plurality of apertures of the collimator assembly comprises a plurality of pinhole apertures.

22. A method for imaging a region of interest with a positron emission tomography (PET) scanner comprising:
    positioning a collimation assembly such that the collimation assembly is closer to the region of interest than a detector associated with the PET scanner, the collimation assembly comprising a plurality of apertures;
    detecting a set of pairs of coincident photons at the detector associated with the PET scanner to determine a corresponding set of lines of response;
    rejecting at least one line of response of the set of respective lines of response according to the relationship of each line of response to the plurality of apertures, such that at least one line of response is rejected according to at least one of a distance from an aperture of the plurality of apertures and an angle of incidence of the at least one line of response with respect to an orientation of the aperture; and
    creating an image based on a plurality of lines of response that have not been rejected.

23. The method of claim 22, wherein the plurality of apertures of the collimator assembly comprises a plurality of pinhole apertures.

24. A method for imaging a region of interest with a positron emission tomography (PET) scanner comprising:
    positioning a collimation assembly such that the collimation assembly is closer to the region of interest than a detector associated with the PET scanner, the collimation assembly comprising a plurality of apertures;
    detecting a set of pairs of coincident photons at the detector associated with the PET scanner to determine a corresponding set of lines of response;
    rejecting at least one line of response of the set of respective lines of response according to the relationship of each line of response to the plurality of apertures, such that at least one line of response is rejected according to a difference in a detection time between a first photon of a corresponding pair of coincident photons and a second photon of the pair of coincident photons; and
    creating an image based on a plurality of lines of response that have not been rejected.

25. The method of claim 24, wherein the plurality of apertures of the collimator assembly comprises a plurality of pinhole apertures.

* * * * *